United States Patent [19]

von Werner et al.

[11] Patent Number: 4,751,027

[45] Date of Patent: Jun. 14, 1988

[54] PROCESS FOR THE PREPARATION OF PERFLUOROCARBOXYLIC ACIDS

[75] Inventors: Konrad von Werner, Halsbach; Anton Probst, Burgkirchen, both of Fed. Rep. of Germany

[73] Assignee: Hoechst Aktiengesellschaft, Frankfurt am Main, Fed. Rep. of Germany

[21] Appl. No.: 939,572

[22] Filed: Dec. 9, 1986

[30] Foreign Application Priority Data

Feb. 26, 1986 [DE] Fed. Rep. of Germany ....... 3606174

[51] Int. Cl.$^4$ .............................................. C07C 51/16
[52] U.S. Cl. ..................................... 260/408; 562/541; 562/605
[58] Field of Search .................. 260/408; 562/541, 605

[56] References Cited

U.S. PATENT DOCUMENTS

| | | | |
|---|---|---|---|
| 4,138,417 | 2/1979 | Ukihashi et al. | 260/406 |
| 4,221,734 | 9/1980 | Commeyras et al. | 260/408 |
| 4,321,209 | 3/1982 | Chan et al. | 260/408 |
| 4,346,235 | 8/1982 | Sonoda et al. | 562/605 X |
| 4,400,325 | 8/1983 | von Werner et al. | 260/408 |

OTHER PUBLICATIONS

Chemical Abstracts, vol. 70, (1969), Abstract No. 77334q, (Abstract of Japanese Publ. Appl. 68-29129).
Journal of Fluorine Chemistry, 13, (1979), 175-177.
Journal of Fluorine Chemistry, 17, (1981), 423-439.

*Primary Examiner*—Werren B. Lone
*Assistant Examiner*—Vera C. Clarke

[57] ABSTRACT

A process is described for the preparation of perfluorocarboxylic acids by oxidizing perfluoroalkylalkenes with permanganate in aqueous solution, catalytic amounts of at least one quaternary ammonium salt containing alkyl and/or arylalkyl groups being added. It is possible by these means to prepare even perfluorocarboxylic acids having a fairly long chain in a high state of purity in a readily controllable reaction and in a good space-time yield.

9 Claims, No Drawings

PROCESS FOR THE PREPARATION OF PERFLUOROCARBOXYLIC ACIDS

The invention relates to a process for the preparation of perfluorinated aliphatic carboxylic acids, as claimed in patent claim 1.

Various methods are known for obtaining perfluorocarboxylic acids. The electrofluorination of carboxylic acid chlorides or fluorides has been described, for example, by D. Lines and H. Sutcliffe; J. Fluorine Chem. 17 (1981) page 423, and in the literature quoted therein. In the case of fairly long-chain acids, however, it gives poor yields because of the competing formation of perfluorinated ethers and alkanes. The oxidation of iodoperfluoroalkanes with oleum disclosed in U.S. Pat. No. 4,400,325 admittedly gives high yields, but requires special working-up in order to recover iodine. The preparation of perfluorocarboxylic acids from iodoperfluoroalkanes, zinc and carbon dioxide is disclosed in U.S. Pat. No. 4,221,734; this process is only successful in aprotic solvents after an involved activation of the zinc. The oxidation of alkenes of the formula $R_fCH=CH_2$ with ozone is described in U.S. Pat. No. 4,138,417; this process is complicated, since it requires the initially formed mixture of perfluorinated aldehydes and ozonides to be treated with a further oxidizing agent. According to C. Guizard and C.G. Beguin; J. Fluorine Chem. 13 (1979) page 175 the oxidation of olefins of the formula $R_fCH=CH_2$ can also be carried out with various oxidizing agents using ruthenium dioxide as catalyst, but in this case an involved recovery of the expensive catalyst is necessary.

The preparation of β-bromotetrafluoropropionic acid from 3,3,4,4-tetrafluoro-4-bromo-1-butene using potassium permanganate and water is described in Japanese Published Specification (Kokoku) 68-29,129. If this process is applied to alkenes containing a fairly long perfluorinated alkyl chain, the reaction takes place in an uncontrollable manner, i.e. at first no reaction takes place, but later the reaction starts, but so violently that it can no longer be controlled, as shown by a subsequent comparison experiment. Although this difficulty can possibly be reduced in some cases by using greatly diluted aqueous permanganate solutions, long reaction times are then required and only an extremely unfavorable space-time yield can be achieved.

A process has now been found which makes it possible to produce, in particular, fairly long-chain perfluorinated aliphatic carboxylic acids from the corresponding perfluoroalkylethylenes in a reaction which proceeds smoothly and can be controlled easily, and in comparatively good space-time yields. This is a process for the preparation of perfluorocarboxylic acids by oxidizing perfluoroalkylethylenes with permanganate in aqueous solution, if appropriate at an elevated temperature, which comprises reacting 1/p mol of a compound of the formula

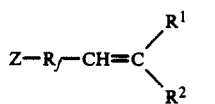

(1)

in which $R_f$ denotes a linear or branched perfluoroalkylene group having 6 to 18 carbon atoms;

Z is F, Cl, Br or

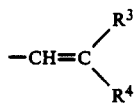

and $R^1$, $R^2$, $R^3$ and $R^4$ are each a hydrogen atom or an alkyl group having 1 to 5 carbon atoms and moreover p is the number of double bonds in the molecule of formula I, in the presence of 0.001 to 0.1 mol of at least one quaternary ammonium salt containing alkyl and/or arylalkyl groups, acidifying the mixture after the completion of the reaction, removing the manganese-IV oxide formed or bringing it into solution by reduction to the manganese-II salt, and separating of and, if necessary, purifying further the resulting perfluoromonocarboxylic or perfluorodicarboxylic acid.

$R_f$ in the compound of the formula I can be a linear or branched perfluoroalkylene group. In the sense of the invention, cyclic perfluoroalkylene groups are also branched. If these groups contain more than 18 carbon atoms, the starting materials are more difficult of access, the reaction time increases and the working-up of the reaction mixture frequently becomes more difficult. If $R_f$ is a perfluoroalkylene group having less than 6 carbon atoms, the reaction according to the invention can also be used, but with less advantage compared with methods according to the known state of the art. Because of the easy accessibility of the starting materials and usability of the perfluorocarboxylic acids produced, compounds of the formula I in which $R_f$ contains 6 to 10 carbon atoms are preferred. The same also applies to compounds of the formula I in which Z is F, Cl or Br. It is also preferable to employ compounds of the formula I in which $R^1$, $R^2$ and, if present, $R^3$ and $R^4$ are each a hydrogen atom or a methyl or ethyl group, particularly good results being achieved if the radicals mentioned are hydrogen atoms.

If p is the number of double bonds in the molecule of the formula I, the reaction is carried out in the presence of 0.001 to 0.1 mol of at least one quaternary ammonium salt containing alkyl and/or arylalkyl groups per 1/p mol of the compound of the formula I. At less than 0.001 mol of quaternary ammonium salt, the reaction ceases to be controllable or has to be carried out at a very great dilution, as a result of which the space-time yield becomes very unfavorable. Although more than 0.1 mol of quaternary ammonium salt per 1/p mol of the compound of the formula I can be used, no additional effect which would reward the increased expense is observed as a result of this. It is preferable to carry out the reaction within the range from 0.01 to 0.05 mol of quaternary ammonium salt.

Examples of suitable quaternary ammonium salts are salts containing 4 identical alkyl or arylalkyl groups, such as, for example, tetrabutylammonium, tetrahexylammonium or tetrabenzylammonium salts or salts containing one fairly long-chain alkyl radical and three identical short-chain alkyl radicals, such as, for example, palmityltrimethyl or lauryltriethyl salts. Particularly good results are obtained if the quaternary ammonium salt employed is at least one of the compounds of the formulae $[(R^5)_2(R^6)_2N]^+X^-$ and $[(R^5)_3R^6N]^+X^-$, the symbols in these formulae having the following meanings: $R^5$ denotes an alkyl or arylalkyl radical having 8 to 20 carbon atoms; $R^6$ denotes an alkyl radical having 1 to 3 carbon atoms and $X^-$ denotes the 1/mth part of an m-valent ion selected from the group comprising $Cl^-$, $Br^-$, $R^8SO_4^-$, $SO_4^{2-}$; $PO_4^{3-}$; $R^8PO_4^{2-}$; $(R^8)_2POhd\ 4^{1-}$; $R^7SO_3^{1-}$; $R^7PO_3^{2-}$; or $(R^7)_2PO_3^{1-}$; in which $R^7$ denotes alkyl having 1 to 4 carbon atoms and $R^8$ denotes H or alkyl having 1 to 4 carbon atoms. Instead of the salt-forming anions mentioned, it is also possible to use other anions, preferably those of inorganic acids which are not oxidized by permanganate ions. It is also possible to use mixtures of several quaternary ammonium salts.

The compound of the formula I, mixtures of several compounds of this formula are also suitable, is oxidized with permanganate in aqueous solution. It is preferable to employ, for this purpose, permanganates which are soluble in water, i.e. those which dissolve to the extent of at least 0.5 g in 1 dm³ of water at 20° C. The permanganates of metals of the first and second group of the periodic system of the elements are primarily suitable for this purpose, because they can be obtained easily and cheaply, especially sodium permanganate or potassium permanganate.

The reaction is carried out at 10° to 100° C. Cooling below 10° C. is generally not necessary, additionally the reaction proceeds unnecessarily slowly at lower temperatures. At over 100° C. undesirable side-reactions take place to an increasing extent, and it would also be necessary, as a result of using pressure-resistant equipment, to incur an expense which otherwise is only necessary in special cases, when low-boiling solvents are used concomitantly. It is preferable to carry out the reaction at 20° to 60° C.

It is not necessary to use sufficient water to dissolve all the permanganate. In general, it is entirely sufficient to use 1 to 10 grams, preferably 2 to 5 grams, of water per gram of compound of the formula I employed. An undissolved deposit of permanganate which may be present at the start of the reaction subsequently dissolves during the reaction. The result of keeping the reaction mixture in agitation, for example by stirring, is to promote the subsequent dissolving process and the achievement, through cooling, of a uniform temperature in the reaction mixture. Although an amount of water greater than 10 g per 1 g of compound of the formula I can be used, the space-time yield is thereby impaired without advantageous effects which would compensate for this disadvantage being observed.

The amount of permanganate to be used depends on the nature of the compound of the formula I. If, in the latter compound, Z denotes F, Cl or Br and $R^1$ and $R^2$ denote H, it is preferable to use at least 10 mol of permanganate ions per 3 mol of this compound. If, on the other hand, Z in the compound of the formula I denotes $-CH=CH_2$ and $R^1$ and $R^2$ denote H, it is preferable to employ at least 20 mol of permanganate ions per 3 mol of this compound.

If, in the compound of the formula I, Z denotes F, Cl or Br and $R^1$ and $R^2$ denote alkyl having 1 to 5 carbon atoms, it is preferable to employ at least 2 mol of permanganate ions per 1 mol of this compound. If, on the other hand, Z in the compound of the formula I is

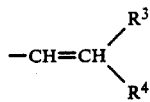

and $R_1$, $R^2$, $R^3$ and $R^4$ are identical with one another or are different and are alkyl having 1 to 5 carbon atoms, it is preferable to employ 4 mol of permanganate ions per 1 mol of this compound.

In all the cases mentioned, the amount of permanganate ions can be greater, but should, in general, not exceed 1.5 times the minimum amount mentioned, otherwise the reaction becomes more expensive unnecessarily and side reactions are also favored. Particularly good results are obtained if the amount of permanganate ions does not exceed 1.3 times the minimum amount mentioned earlier in the text.

Apart from water, no further solvent is generally required for the reaction according to the invention. In special cases, for example if the compound of the formula I is not liquid under the reaction conditions chosen, it can be advantageous to use concomitantly solvents which are not oxidizable by permanganate ions, in order to convert the compound of the formula I completely or partly into the liquid state. Examples of suitable solvents of this type are lower hydrocarbons in which the hydrogen atoms have been replaced completely or to a very large extent by fluorine or chlorine atoms, it being also possible for fluorine and chlorine atoms to occur together in a molecule, subject to the proviso that these lower halogenated hydrocarbons have a boiling point under normal atmospheric pressure of at least 30° C. Examples which may be mentioned are methylene dichloride, chloroform or 1,1,2-trifluoro-1,2,2-trichloroethane.

In most cases the new reaction is carried out under normal atmospheric pressure. As already mentioned above, it can be necessary to carry out the reaction under the autogenous pressure of the reaction mixture, which can be up to about 1 mPa, if appropriate solvents and reaction temperatures in the upper range are used.

The duration of the reaction depends on the reactants and on the temperature selected. In general, the reaction is complete after 0.5 to 15 hours, preferably after 1 to 8 hours.

If very pure starting substances, in particular a carefully purified compound of the formula I, are used for the reaction, the manganese-IV oxide is produced in a readily filterable form and can be removed from the reaction mixture by hot filtration after the completion of the reaction. If a compound of the formula I of only technical purity is used, the filtration of the manganese-IV oxide often causes difficulties, so that it is preferably reduced in acid solution at a pH of 0 to 6.5 to give a water-soluble manganese-II compound. Sulfuric acid or phosphoric acid, for example, are suitable for obtaining and maintaining the acid reaction. Examples of reducing agents used are sulfites, phosphites, phosphorous acid, oxalic acid or formic acid; it is preferable to use sulfur dioxide, since it is cheap, reacts smoothly and does not cause any problems on account of excessive foam formation. Sulfur dioxide can be used in the form of gas or can be formed in the reaction mixture.

After the manganese-IV oxide has been filtered off hot or converted into a water-soluble manganese-II compound, the perfluoroalkanecarboxylic acid produced is separated off from the reaction mixture. In the case of carboxylic acids which are sparingly soluble in water, this can be effected by merely filtering off or merely removing the organic phase, the filter residue or the liquid organic phase being washed with acidified water. The yield can be improved by extracting the combined aqueous phases with a suitable, water-immiscible solvent or solvent mixture. Further amounts of perfluoroalkanecarboxylic acid are obtained after the solvent(s) has/have been evaporated off. Examples of suitable solvents are hydrocarbons containing fluorine and/or chlorine or bromine and having 1 to 3 carbon atoms, but containing not more than 1 hydrogen atom per carbon atom, dialkyl ethers having a total of 4 to 8 carbon atoms, or water-immiscible ketones. If the perfluoroalkanecarboxylic acid produced is readily soluble in water, it is preferable to evaporate the reaction mixture to dryness after removal or reduction of the manganese-IV oxide, if necessary to acidify the residue, for example with sulfuric acid, and to separate off and isolate the perfluoroalkanoic acid by distillation or, as described above, by extraction.

The purity of the perfluoroalkylcarboxylic acid thus obtained is adequate for many end uses. If necessary, it can be purified further by customary methods, such as, for example, fractional distillation, if appropriate under reduced pressure, or recrystallization, for example from toluene or chloroform.

The perfluoroalkylcarboxylic acids produced in accordance with the invention and, in particular, their salts, such as alkali metal or ammonium salts, can be used for many purposes, for example as surfactants for the polymerization of, in particular, fluorine-containing monomers, as fluxes for soldering and as lubricants. They are also used as precursors for the preparation of perfluorinated compounds for fire-extinguishing substances.

As already mentioned initially, the process according to the invention makes it possible to prepare perfluoroalkylcarboxylic acids, even having fairly long chain lengths, in a smooth and readily controllable reaction, in a high state of purity and in good space-time yields.

The examples below are intended to illustrate the invention in greater detail: the perfluoroalkylcarboxylic acids produced are identified by $^{19}F$ nuclear magnetic resonance and by comparison with corresponding compounds which have been prepared according to the state of the art from a perfluoroalkyl iodide by reaction with magnesium, followed by reaction with carbon dioxide and hydrolysis. In some cases, the perfluoroalkylcarboxylic acids are converted into their methyl esters and are subjected to analysis by gas chromatography.

EXAMPLE 1

125 g (0.8 mol) of potassium permanganate are added, with stirring, to a solution of 4.0 g (0.01 mol) of trioctylmethylammonium chloride in 200 cm$^3$ of demineralized water in a laboratory apparatus made of glass. 70.6 g (0.2 mol) of perfluorohexylethylene are added dropwise slowly, with vigorous stirring. Hence 12 mol of permanganate ions are used for 3 mol of the compound of the formula I. The temperature has risen to 40° C. 15 minutes after the start of the addition; the temperature of the reaction mixture is kept at 40° to 45° C. by external cooling, until, after 2.5 hours, all of the perfluorohexylethylene has been metered in. The mixture is then stirred for a further 30 minutes and then heated to 70° C. and filtered through a heated pressure filter. The filter cake is washed with 100 cm$^3$ of hot water, and the combined filtrates are evaporated to dryness on a rotary evaporator. 200 cm$^3$ of concentrated sulfuric acid are added cautiously to the solid thus obtained in a distillation apparatus, in the course of which initially foaming takes place as the result of carbon dioxide evolution. 70.5 g of perfluoroheptanoic acid are obtained by distillation at 1,300 Pa (boiling point = 75° to 76° C.). The yield is 96.8%; the purity (determined by gas chromatography) is 99.8%. The product solidifies on cooling to room temperature.

EXAMPLE 2

68 g (0.43 mol) of potassium permanganate are added, with stirring, to a solution of 1.83 g (0.004 mol) of didecyldimethylammonium methosulfate in 200 cm$^3$ of demineralized water in a laboratory apparatus made of glass. 74.8 g (0.2 mol) of $C_6F_{13}$—CH=C(CH$_3$)$_2$ are added dropwise, with vigorous stirring. 2.15 mol of permanganate ions are used per mol of the compound of the formula I. The further procedure is as described under Example 1, 69.75 g of perfluoroheptanoic acid being obtained (yield 95.8%).

EXAMPLE 3

109 g (0.69 mol) of potassium permanganate are added, with stirring, to a solution of 1.82 g (0.004 mol) of didecyldimethylammonium bisulfate in 200 cm$^3$ of demineralized water in a laboratory apparatus made of glass. 79.22 g (0.2 mol) of $(CF_3)_2CF$—$(CF_2)_4$—CH=CH$_2$ are added dropwise, in the course of 3 hours and with vigorous stirring, with the reaction mixture at a temperature of 40° C. 10.35 mol of permanganate ions are used for 3 mol of the compound of the formula I. After the 3 hours, the mixture is acidified, with continued stirring, by the cautious addition of 65 cm$^3$ of concentrated sulfuric acid. 500 cm$^3$ of a cold saturated sodium sulfite solution, followed by 150 g of sodium sulfite hydrate, are then added, and the mixture is stirred at 90° C. until all the manganese-IV oxide has gone into solution. The lower, organic phase is separated off and the aqueous phase is cooled to room temperature and extracted by shaking with diethyl ether. Evaporating the ether extract gives 50.8 g of residue, which is combined with the organic phase and, after 50 cm$^3$ of concentrated sulfuric acid have been added, is distilled. 77.35 g of $(CF_3)_2CF$—$(CF_2)_4$—COOH having a boiling point of 83° to 84° C. at 1,300 Pa are obtained in the form of a colorless liquid. This corresponds to a yield of 93.4%. The product is 99.2% pure.

EXAMPLE 4

The procedure is as in Example 3, with the following differences: instead of 200 cm$^3$ of water 300 cm$^3$ are used and instead of the compound of the formula $(CF_3)_2CF$—$(CF_2)_4$—CH=CH$_2$ 110.6 g (0.2 mol) of perfluorodecylethylene are used. This means 10.65 mol of permanganate ions for 3 mol of the compound of the formula I. Instead of 40° C., the reaction is carried out at a reaction mixture temperature of 50° to 55° C. for 3 hours. After adding sulfuric acid and reacting the manganese-IV oxide with sulfite as described in Example 3, the mixture is cooled to room temperature and the white, solid crude acid is filtered off from the pink solution and washed with 100 cm$^3$ of cold water. After 50 cm$^3$ of concentrated sulfuric acid have been added, the product is sublimed under a pressure of 1,500 Pa and a temperature of 132° to 135° C. 99.1 g of perfluoroundecanoic acid are obtained as a white solid of melting point 103° to 104° C. This corresponds to a yield of 87.8%.

EXAMPLE 5

15.25 g (0.049 mol) of dioctyldimethylammonium chloride are dissolved in 4,250 cm³ of demineralized water in a rubber-coated kettle of capacity 10 dm³, equipped with a rubber-coated stirrer, and 1,354 g (8.57 mol) of potassium permanganate are added. The mixture is stirred for 10 minutes and then warmed to 40° C. 1,225 g of technical perfluorooctylethylene (impurities: 9.0% by weight of $C_{10}F_{21}H$ and 1.5% of other fluorine compounds), containing 2.46 mol of perfluorooctylethylene, are then metered in, at a stirrer speed of 600 r.p.m., in the course of 5 hours, during which the temperature of the reaction mixture is kept at 55° C. by cooling. 10.45 mol of permanganate ions are used for 3 mol of the compound of the formula I. Stirring is continued for a further hour, but after 30 minutes no further cooling is required to keep the temperature at 55° C. 1,285 g of 96% strength sulfuric acid are then added, with stirring, sufficiently slowly for the foam produced by evolution of carbon dioxide not to climb excessively high in the kettle. 650 g of sulfur dioxide gas are then introduced into the gas space of the kettle in the course of 3.5 hours, with continued stirring and with the exit gas valve closed, the temperature of the mixture being kept at 45° C. by cooling. After stirring for a further 30 minutes the manganese-IV oxide has been reduced completely. The exit gas valve is then opened and a stream of nitrogen at 30 dm³ per hour is passed into the kettle, while the contents of the kettle are heated to 80° to 90° C. at a stirrer speed of 300 r.p.m. A pause of 15 minutes is made after the heating and the stirrer have been switched off, and the liquid lower organic phase, which is still at approx. 70° C., is separated off. It is mixed with 350 g of concentrated sulfuric acid and distilled in vacuo through a column. The boiling point is 110° to 111° C. under a pressure of 2,400 Pa. 970 g of solid perfluorononanoic acid of melting point 57° to 59° C. are obtained. The yield is 85.0%. According to analysis by gas chromatography, the product consists of 99.3% of perfluorononanoic acid and 0.7% of perfluorooctanoic acid.

EXAMPLE 6

110.6 g (0.7 mol) of potassium permanganate are added, with stirring, to a solution of 0.61 g (0.002 mol) of dioctyldimethylammonium chloride in 100 cm³ of demineralized water in a laboratory apparatus made of glass. 35.4 g (0.1 mol) of 3,3,4,4,5,5,6,6,7,7,8,8-dodecafluoro-1,9-decadiene are then added dropwise slowly in the course of one hour, with vigorous stirring. 21 mol of permanganate ions are used for 3 mol of the compound of the formula I. The temperature of the reaction mixture is kept at 20° C. by cooling with ice water, and the mixture is then stirred for a further hour at room temperature. It is then warmed to 50° C. and the manganese-IV oxide formed is filtered off, with suction. The filter cake is stirred with 100 cm³ of water at 80° C. and is again filtered off with suction. The combined filtrates are acidified by adding sulfuric acid cautiously until a pH of 1 has been reached, and are cooled to 20° C. and extracted by shaking with 6 times 100 ml of diethyl ether. The combined ether extracts are immediately freed from ether as completely as possible on a rotary evaporator. This should be carried out as rapidly as possible, since, on prolonged standing in ether solution, perfluorodicarboxylic acids pass over into their ethyl esters with ether cleavage. 50 cm³ of concentrated sulfuric acid are added to the residue, and the mixture is subjected to short path distillation under a pressure of 2 Pa. 10 cm³ of anhydrous sulfuric acid are added to the product thus obtained, and the mixture is sublimed under a pressure of 0.1 Pa with complete exclusion of moisture. 30.5 g of dodecafluorohexane-1,6-dicarboxylic acid are obtained as a white solid which has a melting point of 142° to 144° C. and is extremely hygroscopic. The yield is 78.2%.

COMPARISON TEST A

It is intended to attempt to prepare perfluorononanoic acid analogously to the method disclosed in Japanese Published Specification 68-29,129. For this purpose, perfluorooctylethylene is added dropwise, with vigorous stirring, to a hot mixture, at 90°, of 55.44 g (0.35 mol) of potassium permanganate and 150 cm³ of demineralized water in a stirred apparatus of capacity 500 cm³, equipped with a reflux condenser. At first no detectable reaction takes place. After about 15 g of the perfluorooctylethylene have been added, the reaction suddenly starts so violently that the contents of the flask are rapidly forced into the open through the condenser. The experiment is therefore discontinued.

Differential thermoanalysis of a mixture of potassium permanganate, water and perfluorooctylethylene in a ratio by weight of 1.12:3.81:1 does not indicate an exothermic reaction until 400° C.

We claim:

1. A process for the preparation of perfluorocarboxylic acids by oxidizing perfluoroalkylethylenes with permanganate in aqueous solution, at normal temperature or at an elevated temperature, which comprises reacting 1/p mol of a compound of the formula

in which $R_f$ denotes a linear or branched perfluoroalkylene group having 6 to 18 carbon atoms;

Z denotes F, Cl, Br or

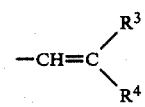

and $R^1$, $R^2$, $R^3$ and $R^4$ each denote a hydrogen atom or an alkyl group having 1 to 5 carbon atoms, and moreover p is the number of double bonds in the molecule of the formula I, in the presence of 0.001 to 0.1 mol of at least one quaternary ammonium salt containing alkyl and/or arylalkyl groups at 10° to 100° C., acidifying the mixture after the completion of the reaction, removing the manganese-IV oxide formed or bringing it into solution by reduction to give the manganese-II salt, and separating off and, if required, purifying further, the resulting perfluoromonocarboxylic or perfluorodicarboxylic acid.

2. The process as claimed in claim 1, wherein sodium permanganate and/or potassium permanganate is employed.

3. The process as claimed in claim 1, wherein a compound of the formula I in which Z denotes F, Cl or Br and $R^1$ and $R^2$ denote H is employed, at least 10 mol of permanganate ions being used for 3 mol of this compound.

4. The process as claimed in claim 1, wherein a compound of the formula I in which Z denotes $-CH=CH_2$ and $R^1$ and $R_2$ denote H is employed, at least 20 mol of permanganate ions being used for 3 mol of this compound.

5. The process as claimed in claim 1, wherein a compound of the formula I in which Z denotes F, Cl or Br and $R^1$ and $R^2$ denote alkyl having 1 to 5 carbon atoms is employed, at least 2 mol of permanganate ions being used for 1 mol of this compound.

6. The process as claimed in claim 1, wherein a compound of the formula I in which Z denotes

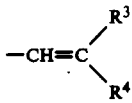

and $R^1$, $R^2$, $R^3$ and $R^4$ are identical with one another or different and denote alkyl having 1 to 5 carbon atoms is employed, at least 4 mol of permanganate ions being used for 1 mol of this compound.

7. The process as claimed in claim 1, wherein at least one compound of the formula

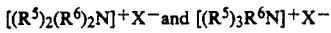

in which
 $R^5$ denotes an alkyl or arylalkyl radical having 8 to 20 carbon atoms,
 $R^6$ denotes an alkyl radical having 1 to 3 carbon atoms and
 $X^-$ denotes the 1/mth part of an m-valent ion selected from the group comprising: $Cl^-$, $Br^-$, $R^8SO_4^-$; $SO_4^{--}$; $PO_4^{---}$; $R^8PO_4^{--}$, $(R^8)_2PO_4^{--}$; $R^7SO_3^-$, $R^7PO_3^{--}$ or $(R^7)_2PO_3^-$
in which
 $R^7$ denotes alkyl having 1 to 4 carbon atoms and
 $R^8$ denotes H or alkyl having 1 to 4 carbon atoms,
is employed as the quaternary ammonium salt.

8. The process as claimed in claim 1, wherein, after the completion of the reaction, the manganese-IV oxide formed is reduced at a pH of 0 to 6.5 in the reaction mixture to give a water-soluble manganese-II compound.

9. The process as claimed in claim 1, wherein the reducing agent used for the manganese-IV oxide is sulfur dioxide, which is added in the form of gas to the reaction mixture or is formed in the reaction mixture.

* * * * *